United States Patent [19]

Ohtsubo et al.

[11] Patent Number: 5,306,499
[45] Date of Patent: Apr. 26, 1994

[54] MICROENCAPSULATED COCKROACH-CONTROLLING COMPOSITION

[75] Inventors: Toshiro Ohtsubo, Hyogo; Shigenori Tsuda, Kyoto; Hitoshi Kawada; Goro Shinjo, both of Osaka; Kozo Tsuji, Nara, all of Japan

[73] Assignee: Sumitomo Chemical Company, Limited, Osaka, Japan

[21] Appl. No.: 613,042

[22] Filed: Nov. 15, 1990

Related U.S. Application Data

[62] Division of Ser. No. 290,384, Dec. 27, 1988, abandoned.

[30] Foreign Application Priority Data

Dec. 25, 1987 [JP] Japan .................. 62-331237

[51] Int. Cl.⁵ .......................................... A01N 25/00
[52] U.S. Cl. ............................... 424/405; 424/408
[58] Field of Search .................. 424/405, 408, 405

[56] References Cited

U.S. PATENT DOCUMENTS

| | | | |
|---|---|---|---|
| 4,670,246 | 6/1987 | Dahl et al. | 424/419 |
| 4,690,786 | 9/1987 | Ninomiya et al. | 264/4.6 |
| 4,822,614 | 4/1989 | Rodero | 424/405 |
| 4,871,766 | 10/1989 | Tsuda et al. | 514/521 |
| 4,889,719 | 12/1989 | Ohtsubo et al. | 424/408 |
| 4,985,413 | 1/1991 | Kohama et al. | 514/79 |

FOREIGN PATENT DOCUMENTS

| | | |
|---|---|---|
| 5538325 | of 0000 | Japan . |
| 54-55726 | 5/1979 | Japan . |
| 59-227806 | 12/1984 | Japan . |
| 62-161706 | 7/1987 | Japan . |
| 2187957 | of 0000 | United Kingdom . |

*Primary Examiner*—Thurman K. Page
*Assistant Examiner*—R. Harrison
*Attorney, Agent, or Firm*—Sughrue, Mion, Zinn, Macpeak & Seas

[57] ABSTRACT

Microencapsulated pyrethroidal cockroach-controlling composition is provided, which has an excellent residual effect. The composition comprises phenylxylylethane and a pyrethroidal compound and is encapsulated in microcapsules formed of a polyurethane wall which have an average particle diameter of not more than 80 μm, a wall thickness of not more than 0.3 μm, and a value of the average particle diameter/wall thickness of 100–400.

6 Claims, No Drawings

MICROENCAPSULATED COCKROACH-CONTROLLING COMPOSITION

This is a divisional of application Ser. No. 07/290,384 filed Dec. 27, 1988, abandoned.

BACKGROUND OF THE INVENTION

The present invention relates to a microencapsulated cockroach-controlling composition wherein an insecticide having a 3-phenoxybenzyl group and phenylxylylethane are encapsulated in microcapsules having polyurethane wall which have an average particle diameter of not more than 80 μm, a wall thickness of not more than 0.3 μm and a value of the average particle diameter/wall thickness of 100–400.

Controlling cockroach has been mainly carried out by a residual spray method.

At present, formulations such as emulsifiable concentrate, solubilized emulsion concentrate and oil solution which contain, for example, an organophosphorus insecticide or pyrethroidal insecticide as an active ingredient are used for the residual spray.

Especially residual efficacy and safety are desired factors to formulations used for the residual spray. If the residual efficacy is to be enhanced with the conventional formulations such as emulsifiable concentrate, solubilized emulsion concentrate and oil solution a high application dosage is required, which may bring about problem in safety. Thus, formulations being safer and having greater in efficacy are increasingly demanded.

Under the circumstances, research and development of so-called microencapsulation technique that an active ingredient is enclosed in a wall material have become intensive. As microencapsulated insecticides, those which contain organophosphorus insecticide as an active ingredient are disclosed in Japanese Patent Kokai No. 62-161706 and those which contain pyrethroidal insecticide as an active ingredient are disclosed in Japanese Patent Kokoku No. 55-38325.

In some cases, microencapsulation of insecticides might be effective for improving residual efficacy.

However, residual efficacy of microencapsulated insecticides varies depending upon a particle diameter of microcapsule and a wall thickness. Optimum particle diameter and wall thickness should be chosen in order to maintain residual efficacy for a prolonged period of time. The optimum range naturally varies depending on varieties of insect pests to be controlled and of insecticides.

In general, microencapsulation of insecticides having a polyurethane wall is performed by interfacial polymerization using a polyfunctional isocyanate.

The interfacial polymerization method essentially requires a step of homogeneously mixing an active ingredient to be enclosed in capsules with polyfunctional isocyanate.

In the case when the active ingredient is a pyrethroidal insecticide, an organic solvent may be added as so-called cosolvent when the insecticide is mixed with a polyfunctional isocyanate which is sometimes high in viscosity, since this insecticide is generally high in viscosity and sometimes is in the form of crystal. Japanese Patent Kokoku No. 55-38325 mentions "For example, as usual organic solvents, there may be selected from hydrocarbons such as xylene, toluene, hexane and heptane, chlorinated hydrocarbons such as carbon tetrachloride and chloroform, ketones such as methylisobutyl ketone, methyl ethyl ketone and cyclohexanone and esters such as diethyl phthalate and n-butyl acetate."

However, these known techniques are not necessarily satisfactory when some pyrethroidal insecticides are used as an active ingredient for cockroach-controlling.

The inventors have made intensive study on optimum ranges of particle diameter and wall thickness of microcapsules and on selection of optimum organic solvents when an insecticide having a 3-phenoxybenzyl group is encapsulated as a core material in a polyurethane wall and then this is used for cockroach-controlling.

As a result, it has been found that some insecticides having a 3-phenoxybenzyl group microencapsulated as a core material in polyurethane wall using phenylxylylethane as a cosolvent have residual efficacy for a prolonged period of time for cockroach-controlling.

SUMMARY OF THE INVENTION

The present invention provides a microencapsulated cockroach-controlling composition which is referred to as "the present composition" hereinafter, wherein phenylxylylethane and at least one active ingredient defined below are encapsulated in a microcapsule having a polyurethane wall which has an average particle diameter of not more than 80 μm, a wall thickness of not more than 0.3 μm and a value of the average particle diameter/wall thickness of 100–400. The active ingredients mentioned above are those represented by the formula:

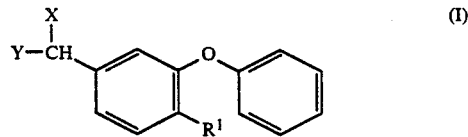

wherein $R^1$ represents a hydrogen atom or a fluorine atom, X represents a hydrogen atom or a cyano group, and Y represents a group represented by the formula:

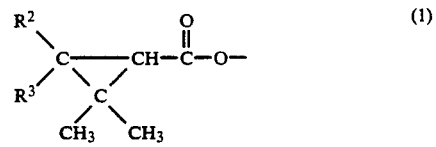

wherein $R^2$ represents a hydrogen atom or a methyl group; when $R^2$ is a hydrogen atom, $R^3$ represents a group of the formula

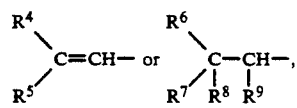

in which $R^4$ represents a methyl group, a chlorine atom, a bromine atom or a fluorine atom, $R^5$ represents a methyl group, a trifluoromethyl group, a chlorine atom, a bromine atom or a fluorine atom and $R^6$, $R^7$, $R^8$ and $R^9$ are the same or different and each represents a chlorine atom, a bromine atom or a fluorine atom, and when $R^2$ is a methyl group, $R^3$ represents a methyl group, a group represented by the formula:

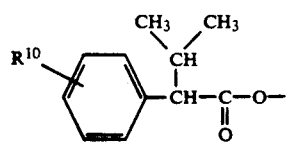

wherein $R^{10}$ represents a chlorine atom, a bromine atom, a fluorine atom, a trifluoromethoxy group, a difluoromethoxy group or a 3,4-methylenedioxy group, or a group represented by the formula:

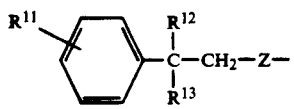

wherein Z represents an oxygen atom or a —$CH_2$— group, $R^{11}$ represents a lower alkoxyl group (e.g., $C_1$-$C_5$ alkoxyl group), a chlorine atom, a bromine atom or a fluorine atom, $R^{12}$ represents a hydrogen atom or a lower alkyl group (e.g., $C_1$-$C_2$ alkyl group) and $R^{13}$ represents a lower alkyl group (e.g., $C_1$-$C_2$ alkyl group) or a trifluoromethyl group.

DESCRIPTION OF THE INVENTION

Cockroaches to which the present composition is applied include, for example, American cockroach (*Periplaneta americana*), brown cockroach (*Periplaneta brunnea*), smokybrown cockroach (*Periplaneta fuliginosa*), *Nauphaeta cinerea* and German cockroach (*Blattella germanica*).

Phenylxylylethane, one of the essential elements of the present invention, is found among cosolvents for preparing homogeneous solution of active ingredient (I) and polyfunctional isocyanate when a polyurethane wall is prepared by an interfacial polymerization method.

As cosolvents, there may be used various organic solvents as disclosed in Japanese Patent Kokoku No. 55-38325, but those which are high in flash point and less in irritating smell are preferred from a viewpoint of safety and prevention of disaster.

Table 1 shows flash point and degree of smell of various organic solvents disclosed in Japanese Patent Kokoku No. 55-38325 and phenylxylylethane used in the present invention. Clearly, phenylxylylethane is so high in flash point and so weak in smell that it is especially suitable for use as a cosolvent. Furthermore, when phenylxylylethane is compared with diethyl phthalate, the former is preferred to the latter in cost and safety.

Table 1

TABLE 1

| Name of organic solvent | Flash point (°C.) | Degree of smell |
|---|---|---|
| Xylene | 25 | Strong |
| Toluene | 4 | " |
| Hexane | −26 | " |
| Heptane | −4 | " |
| Carbon tetrachloride | — | " |
| Chloroform | — | " |
| Methylisobutyl ketone | 23 | " |
| Methyl ethyl ketone | −1 | " |
| Diethyl phthalate | 152 | Weak |
| n-Butyl acetate | 22 | Middle |
| Phenylxylylethane | 152 | Weak |

Surprisingly, the microencapsulated composition of the active ingredient (I) prepared using the phenylxylylethane as a cosolvent has residual efficacy for cockroach-controlling superior to that of the microencapsulated composition of the active ingredient (I) prepared using other organic solvents such as methyl isobutyl ketone and cyclohexanone or without using any organic solvent.

When the microencapsulated composition of the active ingredient (I) having polyurethane wall is used for cockroach-control, residual efficacy against cockroach is able to be retained for a prolonged period of time only by microencapsulating the active ingredient (I) and phenylxylylethane in a microcapsule having a polyurethane wall which has an average particle diameter of not more than 80 μm, a wall thickness of not more than 0.3 μm and a value of the average particle diameter/wall thickness of 100–400.

The microencapsulation is performed, for example, by the method that a hydrophobic solution containing a polyfunctional isocyanate, active ingredient (I) and phenylxylylethane is dispersed in an aqueous solution containing a water-soluble polymer as a dispersing agent in the form of droplets and then polymerization reaction with a polyhydric alcohol having at least two hydroxy groups is allowed to run. After the encapsulation reaction is over, the resulting capsule suspension as such is diluted with water so as to obtain a desired concentration and, if necessary, a suspension stabilizer is added to obtain a stable slurry formulation.

As the polyhydric alcohols having at least two OH groups, mention may be made of, for example, ethylene glycol, propylene glycol, butylene glycol, hexanediol, heptanediol, dipropylene glycol, triethylene glycol, glycerin, resorcin and hydroquinone. As the polyfunctional isocyanate, mention may be made of, for example, toluene diisocyanate, hexamethylene diisocyanate, adducts of toluene diisocyanate and trimethylolpropane, self-condensates of hexamethylenediisocyanate, SUMIDUR L ® (made by Sumitomo-Bayer Urethane Co., Ltd.) and SUMIDUR N ® (made by SumitomoBayer Urethane Co., Ltd.).

The dispersing agents used for dispersing a hydrophobic solution containing active ingredient (I), phenylxylylethane and polyfunctional isocyanate include, for example, natural polysaccharides such as gum arabic, semi-synthetic polysaccharides such as carboxymethyl cellulose and methyl cellulose, synthetic polymers such as polyvinyl alcohol and fine mineral powders such as magnesium aluminum silicate. They may be used alone or in combination of two or more. When dispersibility is weak, this may be improved by adding a known surfactant such as given in H. Horiguchi, "Synthetic Surface Active Agent".

As suspension stabilizers for capsule slurry, the water-soluble polymers enumerated above as dispersing agents may be used as such, but, if necessary, there may be used, as thickening agents, one or more of natural polysaccharides such as xanthane gum and locust bean gum, semi-synthetic polysaccharides such as carboxymethyl cellulose, synthetic polymers such as sodium polyacrylate and fine mineral powders such as magnesium aluminum silicate.

The active ingredient (I) used in the present invention includes geometrical isomers and further includes optical isomers resulting from the presence of asymmetric carbon and further includes mixtures thereof.

Typical examples of the active ingredients (I) are as follows.

(RS)-α-cyano-3-phenoxybenzyl (RS)-2-(4-chlorophenyl)-3-methylbutyrate (fenvalerate), (S)-α-cyano-3-phenoxybenzyl (S)-2-(4-chlorophenyl)-3-methylbutyrate (esfenvalerate), (RS)-α-cyano-3-phenoxybenzyl 2,2,3,3-tetramethylcyclopropanecarboxylate (fenpropathrin), 3-Phenoxybenzyl (1R)-cis, trans-chrysanthemate (d-phenothrin), (RS)-α-cyano-3-phenoxybenzyl (1R)-cis,transchrysanthemate (cyphenothrin), 3-Phenoxybenzyl (1RS)-cis,trans-3-(2,2-dichlorovinyl)-2,2-dimethylcyclopropanecarboxylate (permethrin), α-Cyano-3-phenoxybenzyl (1R)-cis,trans-3-(2,2-dichlorovinyl)-2,2-dimethylcyclopropanecarboxylate (cypermethrin), α-Cyano-3-phenoxybenzyl (1R)-cis,trans-3-(2,2-dibromovinyl)-2,2-dimethylcyclopropanecarboxylate (deltamethrin), 2-(4-Ethoxyphenyl)-2-methylpropyl 3-phenoxybenzyl ether (ethofenprox), and (S)-α-cyano-3-phenoxybenzyl (1R)-cis-2,2-dimethyl3-(1,2,2,2-tetrabromoethyl) cyclopropanecarboxylate (tralomethrin).

If necessary, synergists such as piperonyl butoxide and stabilizers such as BHT (2,6-di-t-butyl-4-methylphenol) may also be optionally added.

When addition amount of phenylxylylethane is too small, development of efficacy is insufficient and when too much, concentration of active ingredient decreases. Therefore, addition amount of phenylxylylethane is usually 0.2–5 parts by weight per part by weight of active ingredient (I).

The average particle diameter of microcapsules is determined depending on varieties and concentration of dispersing agent used for dispersion and on the degree of mechanical agitation during dispersion. For measurement of average particle diameter, the Coulter counter Model TA-II (available from Nikkaki) may be used, for example.

Wall thickness of microcapsule varies depending on volume ratio of a core material to a wall material and is obtained from the following approximate equation.

$$\text{Thickness} = \frac{Ww}{Wc} \times \frac{\rho c}{\rho w} \times \frac{d}{6}$$

wherein
d: Average particle diameter of microcapsules
wc: Weight of core material
Ww: Weight of wall material
ρw: Density of wall material
ρc: Density of core material The wall thickness in the present invention is calculated using the above equation.

The present composition, before being applied to, is usually diluted several times-several hundreds times with water, although it depends on the nominal content of the active ingredient, and then the diluted composition is applied to by a conventional sprayer. Dosage which varies depending on varieties of the active ingredient is usually 10–1000 mg/m² in terms of the active ingredient.

The present invention will be explained in more detail by the following Examples, Comparative Examples and Test Examples.

EXAMPLE 1

Ten gram of "SUMIDUR" L ® (as indicated herebefore) and 100 g of "HISOL" SAS-296 ® (1-phenyl-1-xylylethane made by Nippon Petrochemicals Co.) were added to 100 g of cyphenothrin and stirred until uniform solution was obtained. This solution was added to 350 g of aqueous solution containing 5% by weight of gum arabic as a dispersing agent and stirring was carried out for several minutes by means of "T.K. autohomomixer" (commercial name, Tokushukika Kogyo Co.) at room temperature until microdrops were formed. The revolution rate was 8000 rpm. Then, to the dispersed solution was added 10 g of ethylene glycol and the reaction was allowed to proceed with gently stirring in a constant temperature bath at 60° C. for 24 hours to obtain suspension of a microencapsulated composition.

Water was added to the suspension to make total weight of 1000 g to obtain slurry of microcapsules wherein 10% by weight of cyphenothrin is encapsulated (Present composition (1)).

The resulting microcapsule had an average particle diameter of 20 μm, a wall thickness of 0.11 μm and a ratio of average particle diameter/wall thickness of 182.

EXAMPLE 2

Example 1 was repeated except that amount of "SUMIDUR" L ® (as indicated herebefore) was changed to 6 g, thereby obtaining slurry of microcapsules wherein 10% by weight of cyphenothrin is encapsulated (present composition (2)).

The resulting microcapsules had an average particle size of 19 μm, a wall thickness of 0.06 μm and a ratio of average particle diameter/wall thickness of 317.

EXAMPLE 3

Example 1 was repeated except that amount of "SUMIDUR" L ® (as indicated before) was changed to 8 g and the revolution rate of T.K. autohomomixer (as indicated above) was 6500 rpm, thereby to obtain slurry of microcapsules wherein 10% by weight of cyphenothrin is encapsulated (present composition (3)).

The resulting microcapsules had an average particle diameter of 30 μm, a wall thickness of 0.14 μm and a ratio of average particle diameter/wall thickness of 214.

EXAMPLE 4

Example 1 was repeated except that amount of "SUMIDUR" L ® (as indicated before) was changed to 5 g and the revolution rate of T.K. homomixer (as indicated before) was changed to 4700 rpm, thereby to obtain slurry of microcapsules wherein 10% by weight of cyphenothrin is encapsulated (present composition (4)).

The resulting microcapsules had an average particle diameter of 50 μm, a wall thickness of 0.14 μm and a ratio of average particle diameter/wall thickness of 357.

EXAMPLE 5

Example 4 was repeated except that the revolution rate of T.K. homomixer (indicated above) was changed to 4000 rpm, thereby to obtain slurry of microcapsules wherein 10% by weight of cyphenothrin is encapsulated (present composition (5)).

The resulting microcapsules had an average particle diameter of 70 μm, a wall thickness of 0.20 μm and a ratio of average particle diameter/wall thickness of 350.

EXAMPLE 6

Eight gram of "SUMIDUR" L ® (as indicated before) and 100 g of "HISOL" SAS-296 ® (as indicated before) were added to 100 g of fenvalerate and stirred until uniform solution was obtained. This solution was added to 350 g of aqueous solution containing 5% by weight of gum arabic as a dispersing agent, followed by stirring for several minutes by T.K. homomixer (as indicated before) at a revolution rate of 4700 rpm at room temperature until microdrops were formed. Then, to the dispersed solution was added 10 g of ethylene glycol and the reaction was allowed to proceed with gentle stirring in a constant temperature bath of 60° C. for 24 hours to obtain suspension of microencapsulated composition.

Water was added to the suspension to make total weight of 1000 g to obtain slurry of microcapsules wherein 10% by weight of fenvalerate is encapsulated (present composition (6)).

The resulting microcapsules had an average particle diameter of 50 μm, a wall thickness of 0.22 μm and a ratio of average particle diameter/wall thickness of 227.

EXAMPLE 7

Seven gram of "SUMIDUR" L ® (as indicated before) and 20 g of "HISOL" SAS-296 ® (as indicated before) were added to 100 g of d-phenothrin and stirred until uniform solution was obtained. This solution was added to 200 g of aqueous solution containing 5% by weight of gum arabic as a dispersing agent, followed by stirring for several minutes by T.K. homomixer (as indicated before) at 6400 rpm at room temperature until microdrops were formed. Then, to the dispersed solution was added 12 g of ethylene glycol and the reaction was allowed to proceed with gentle stirring in a constant temperature bath of 70° C. for 18 hours to obtain suspension of microencapsulated composition.

To the suspension was added aqueous solution containing 0.6% by weight of xanthane gum to make total weight of 500 g to obtain slurry of microcapsules wherein 20% by weight of d-phenothrin is encapsulated (present composition (7)).

The resulting microcapsules had an average particle diameter of 30 μm, a wall thickness of 0.2 μm and a ratio of average particle diameter/wall thickness of 150.

EXAMPLE 8

Twelve gram of "SUMIDUR" L ® (as indicated before) and 50 g of "HISOL" SAS-296 ® (as indicated before) were added to 100 g of cyphenothrin and stirred until uniform solution was obtained. This solution was added to 300 g of aqueous solution containing 5% by weight of gum arabic as a dispersing agent, followed by stirring for several minutes by T.K. homomixer (as indicated before) at 8500 rpm at room temperature until microdrops were formed. Then, to the dispersed solution was added 15 g of ethylene glycol and the reaction was allowed to proceed with gentle stirring in a constant temperature bath of 50° C. for 40 hours to obtain suspension of microencapsulated composition.

To the suspension was added aqueous solution containing 20% by weight of neutralized "AGRISOL" FL-100F ® (Kao Soap Co., Ltd.) to make total weight of 1000 g to obtain slurry of microcapsules wherein 10% by weight of cyphenothrin is encapsulated (present composition (8)).

The resulting microcapsules had an average particle diameter of 20 μm, a wall thickness of 0.18 μm and a ratio of average particle diameter/wall thickness of 111.

EXAMPLE 9

Eight gram of "SUMIDUR" L ® (as indicated before) and 150 g of "HISOL" SAS-296 ® (as indicated before) were added to 50 g of fenvalerate and stirred until uniform solution was obtained. This solution was added to 350 g of aqueous solution containing 5% by weight of gum arabic as a dispersing agent, followed by stirring for several minutes by T.K. homomixer (as indicated before) at 6500 rpm at room temperature until microdrops were formed. Then, to the dispersed solution was added 20 g of propylene glycol and the reaction was allowed to proceed with gentle stirring in a constant temperature bath of 60° C. for 24 hours to obtain suspension of microencapsulated composition.

To the suspension was added aqueous solution containing 0.4% by weight of xanthane gum and 0.8% by weight of magnesium aluminum silicate to make total weight of 1000 g to obtain slurry of microcapsules wherein 5% by weight of fenvalerate is encapsulated (present composition (9)).

The resulting microcapsules had an average particle diameter of 30 μm, a wall thickness of 0.13 μm and a ratio of average particle diameter/wall thickness of 231.

EXAMPLE 10

Example 8 was repeated except that 7 g of "SUMIDUR" N ® (as indicated before) was used in place of 12 g of "SUMIDUR" L ® (as indicated before) and the revolution rate was changed to 4700 rpm, thereby to obtain slurry of microcapsules wherein 10% by weight of cyphenothrin is encapsulated(present composition (10)).

The resulting microcapsules had an average particle diameter of 50 μm, a wall thickness of 0.28 μm and a ratio of average particle diameter/wall thickness of 179.

EXAMPLE 11

Example 8 was repeated except that 4 g of "SUMIDUR" L ® (as indicated before) and 4 g of "SUMIDUR" T-80 ® (toluene diisocyanate made by Sumitomo-Bayer Urethane Co., ltd.) were used in place of 12 g of the "SUMIDUR" L ® (as indicated before), thereby to obtain slurry of microcapsules wherein 10% by weight of cyphenothrin is encapsulated (present composition (11)).

The resulting microcapsules had an average particle diameter of 21 μm, a wall thickness of 0.16 μm and a ratio of average particle diameter/wall thickness of 131.

EXAMPLE 12

Ten gram of "SUMIDUR" L ® (as indicated before) and 150 g of "HISOL" SAS-296 ® (as indicated before) were added to 100 g of permethrin and stirred until uniform solution was obtained. This solution was added to 400 g of aqueous solution containing 5% by weight of gum arabic and 3% by weight of ethylene glycol, followed by stirring for several minutes by T.K. homomixer (as indicated before) at 4700 rpm at room temperature until microdrops were formed. Then, the reaction was allowed to proceed with gentle stirring in a constant temperature bath of 70° C. for 18 hours to obtain suspension of microencapsulated composition.

To the suspension was added water to make total weight of 1000 g and this suspension was diluted twice with aqueous solution containing 0.4% by weight of xanthane gum and 1.0% by weight of magnesium aluminum silicate to obtain slurry of microcapsules wherein 5% by weight of permethrin is encapsulated (present composition (12)).

The resulting microcapsules had an average particle diameter of 50 μm, a wall thickness of 0.23 μm and a ratio of average particle diameter/wall thickness of 217.

EXAMPLE 13

Six gram of "SUMIDUR" L ® (as indicated before) and 80 g of "HISOL" SAS-296 ® (as indicated before) were added to 100 g of cypermethrin to obtain uniform solution. This solution was added to 400 g of aqueous solution containing 10% by weight of polyvinyl alcohol as a dispersing agent, followed by stirring for several minutes by T.K. homomixer (as indicated before) at 2700 rpm until microdrops were formed. Then, to the dispersed solution was added 8 g of ethylene glycol and the reaction was allowed to proceed with gentle stirring in a constant temperature bath of 60° C. for 24 hours to obtain suspension of microencapsulated composition.

Water was added thereto to make total weight of 1000 g to obtain slurry of microcapsules wherein 10% by weight of cypermethrin is encapsulated (present composition (13)).

The resulting microcapsules had an average particle diameter of 16 μm, a wall thickness of 0.07 μm and a ratio of average particle diameter/wall thickness of 229.

COMPARATIVE EXAMPLE 1

Twentytwo gram of "SUMIDUR" L ® (as indicated before) and 100 g of "HISOL" SAS-29 ® (as indicated before) were added to 100 g of cyfenothrin to make uniform solution. This solution was added to 400 g of aqueous solution containing 10% by weight of polyvinyl alcohol as a dispersing agent, followed by stirring for several minutes by T.K. homomixer (as indicated before) at 3500 rpm until microdrops were formed. Then, to the dispersed solution was added 20 g of ethylene glycol and the reaction was allowed to proceed with gentle stirring in a constant temperature bath of 60° C. for 24 hours to obtain suspension of microencapsulated composition.

Water was added thereto to make total weight of 1000 g to obtain slurry of microcapsules wherein 10% by weight of cyphenothrin is encapsulated (comparative composition (1)).

The resulting microcapsules had an average particle diameter of 10 μm, a wall thickness of 0.12 μm and a ratio of average particle diameter/wall thickness of 83.

COMPARATIVE EXAMPLE 2

Example 1 was repeated except that amount of "SUMUDUR" L ® (as indicated before) was changed to 3.5 g and the revolution rate of T.K. homomixer was changed to 4700 rpm, thereby to obtain slurry of microcapsules wherein 10% by weight of cyphenothrin is encapsulated (comparative composition (2)).

The resulting microcapsules had an average particle diameter of 50 μm, a wall thickness of 0.1 μm and a ratio of average particle diameter/wall thickness of 500.

COMPARATIVE EXAMPLE 3

Six gram of "SUMIDUR" L ® (as indicated before) was added to 100 g of cyphenothrin to make uniform solution. This solution was added to 400 g of aqueous solution containing 10% by weight of polyvinyl alcohol as a dispersing agent, followed by stirring for several minutes by T.K. homomixer (as indicated before) at 2700 rpm until microdrops were formed. Then, to the dispersed solution was added 6 g of ethylene glycol and reaction was allowed to proceed with gentle stirring in a constant temperature bath of 60° C. for 24 hours to obtain suspension of microencapsulated composition.

Water was added to the suspension to make total weight of 1000 g to obtain slurry of microcapsules wherein 10% by weight of cyphenothrin is encapsulated (comparative composition (3)).

The resulting microcapsules had an average particle diameter of 15 μm, a wall thickness of 0.11 μm and a ratio of average particle diameter/wall thickness of 136.

COMPARATIVE EXAMPLE 4

Example 6 was repeated except that methyl isobutyl ketone was used in place of the "HISOL" SAS-296 ® (as indicated before), thereby to obtain slurry of microcapsules wherein 10% by weight of fenvalerate is encapsulated (comparative composition (4)).

The resulting microcapsules had an average particle diameter of 50 μm, a wall thickness of 0.21 μm and a ratio of average particle diameter/wall thickness of 238.

COMPARATIVE EXAMPLE 5

Example 6 was repeated except that acetophenone was used in place of the "HISOL" SAS-296 ® (as indicated before), thereby to obtain slurry of microcapsules wherein 10% by weight of fenvalerate is encapsulated (comparative composition (5)).

The resulting microcapsules had an average particle diameter of 50 μm, a wall thickness of 0.23 μm and a ratio of average particle diameter/wall thickness of 217.

COMPARATIVE EXAMPLE 6

Example 6 was repeated except that cyclohexanone was used in place of the "HISOL" SAS-296 ® (as indicated before), thereby to obtain slurry of microcapsules wherein 10% by weight of fenvalerate is encapsulated (comparative composition (6)).

The resulting microcapsules had an average particle diameter of 50 μm, a wall thickness of 0.22 μm and a ratio of average particle diameter/wall thickness of 227.

COMPARATIVE EXAMPLE 7

Four gram of "SUMIDUR" L ® (as indicated before) was added to 100 g of heated fenvalerate to make uniform solution. Immediately, this solution was added to 350 g of heated aqueous solution containing 5% by weight of gum arabic as a dispersing agent, followed by stirring for several minutes by T.K. homomixer (as indicated before) at 4800 rpm until microdrops were formed. Then, to the dispersed solution was added 6 g of ethylene glycol and the reaction was allowed to proceed with gentle stirring in a constant temperature bath of 60° C. for 24 hours to obtain suspension of microencapsulated composition.

Water was added to the suspension to make total weight of 1000 g to obtain slurry of microcapsules wherein 10% by weight of fenvalerate is encapsulated (comparative composition (7)).

The resulting microcapsules had an average particle diameter of 50 μm, a wall thickness of 0.23 μm and a ratio of average particle diameter/wall thickness of 217.

TEST EXAMPLE 1

Each of the present composition (6) and comparative compositions (4)–(6) was put in a 100 cc beaker and olfactory test was conducted on whether or not the compositions have smell of a solvent. Ten subjects were employed, to whom no information was given as to the name of solvents used in the preparation of microcapsules. The results are shown in Table 2.

Table 2 (Test on smell of a solvent)

TABLE 2

(Test on smell of a solvent)

| Test composition | Number of persons (subjects) who sensed smell of a solvent |
|---|---|
| Present composition (6) | 1 |
| Comparative composition (4) | 10 |
| Comparative composition (5) | 10 |
| Comparative composition (6) | 10 |

That is, all persons sensed smell of the solvent for comparative compositions in which methyl isobutyl ketone, acetophenone or cyclohexanone was used as a solvent while only one person sensed smell of the solvent for the present composition (6) in which phenylxylylethane was used.

TEST EXAMPLE 2

Each of the test compositions enumerated in Table 3 was diluted twenty times with water and each of the diluted composition was uniformly sprayed on a plywood panel of 15 cm × 15 cm at a rate of 50 ml/m². After the treated plywood panel was dried for 2 hours, a plastic ring of 13 cm in diameter and 5 cm in height (for prevention of escape; inner surface was coated with butter) was placed on the treated panel and a group of ten German cockroaches were confined to contact with the treated panel for 2 hours. The cockroaches were transferred to a plastic cup with water and diet, and mortality was observed after 3 days.

Furthermore, mortality after lapse of 2, 4 and 8 weeks was obtained using the same sprayed surfaces.

Table 3 Mortality of German cockroach (Repeated 3 times)

TABLE 3

Mortality of German cockroach (Repeated 3 times)

| Test composition | Average particle diameter ($\mu$m) | Wall thickness ($\mu$m) | Average particle diameter/wall thickness | Time (week) for treatment with the test composition and mortality (%) after 72 hours | | | |
|---|---|---|---|---|---|---|---|
| | | | | 0 | 2 | 4 | 8 |
| The present composition (1) | 20 | 0.11 | 182 | 100 | 100 | 100 | 100 |
| The present composition (2) | 19 | 0.06 | 317 | 100 | 100 | 100 | 90 |
| The present composition (3) | 30 | 0.14 | 214 | 100 | 100 | 100 | 94 |
| The present composition (4) | 50 | 0.14 | 357 | 100 | 100 | 100 | 83 |
| The present composition (5) | 70 | 0.20 | 350 | 100 | 100 | 100 | 80 |
| Comparative composition (1) | 10 | 0.12 | 83 | 100 | 100 | 70 | 50 |
| Comparative composition (2) | 50 | 0.10 | 500 | 100 | 67 | 47 | 47 |
| Comparative composition (3)* | 15 | 0.11 | 136 | 100 | 87 | 69 | 52 |

*No phenylxylylethane was used.

TEST EXAMPLE 3

Each of the test compositions enumerated in Table 4 was diluted forty times with water and each dilution was applied onto a plywood panel of 15 cm × 15 cm at a rate of 50 ml/m². After the treated panel was dried for 2 hours, a plastic ring of 13 cm in diameter and 5 cm in height (for prevention of escape; inner surface was coated with butter) was placed on the panel and a group of ten German cockroaches were confined to contact with the treated panel for 2 hours. The cockroaches were transferred into a plastic cup with water and diet, and mortality was observed after 3 days.

Furthermore, mortality after treatment for 2, 4 and 8 weeks was obtained using the same applied surfaces.

TABLE 4

Mortality of German cockroach (repeated 3 times)

| Test composition | Average particle diameter ($\mu$m) | Wall thickness ($\mu$m) | Average particle diameter/wall thickness | Solvent used | Time (week) for treatment with composition and mortality (%) after 72 hours | | | |
|---|---|---|---|---|---|---|---|---|
| | | | | | 0 | 2 | 4 | 8 |
| The present composition (6) | 50 | 0.22 | 227 | Phenylxylylethane | 100 | 100 | 100 | 80 |
| Comparative composition (4) | 50 | 0.21 | 238 | Methyl isobutyl ketone | 100 | 90 | 67 | 53 |
| Comparative composition (5) | 50 | 0.23 | 217 | Acetophenone | 100 | 93 | 83 | 53 |
| Comparative composition (6) | 50 | 0.22 | 227 | Cyclohexanone | 100 | 100 | 70 | 67 |
| Comparative | 50 | 0.23 | 217 | — | 100 | 67 | 50 | 43 |

TABLE 4-continued

| | Mortality of German cockroach (repeated 3 times) | | | | | | | |
|---|---|---|---|---|---|---|---|---|
| Test composition | Average particle diameter (μm) | Wall thickness (μm) | Average particle diameter/ wall thickness | Solvent used | Time (week) for treatment with composition and mortality (%) after 72 hours | | | |
| | | | | | 0 | 2 | 4 | 8 |
| composition (7) | | | | | | | | |

We claim:

1. A method for controlling cockroaches comprising: applying a microencapsulated cockroach controlling composition,
   (a) said microcapsules having
      (i) a polyurethane wall,
      (ii) an average particle diameter of not more than 80 microns,
      (iii) a wall thickness of not more than 0.3 microns, and
      (iv) an average particle diameter/wall thickness ratio of 100 to 400; and
   (b) said microcapsules containing phenylxylylethane and at least one insecticidal compound selected from the group consisting of the compounds represented by formula (I)

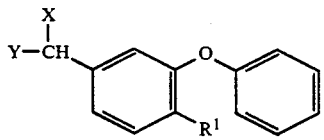

wherein
$R^1$ represents a hydrogen or a fluorine atom,
X represents a hydrogen atom or a cyano group, and
Y represents a group of formula (II), (III), or (IV)

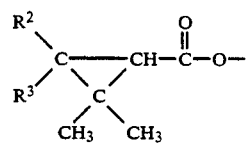

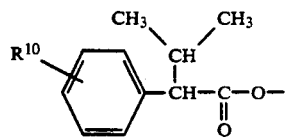

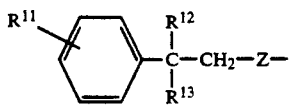

wherein
$R^2$ represents a hydrogen atom or a methyl group; and when $R^2$ is a hydrogen atom, $R^3$ represents a group of formula

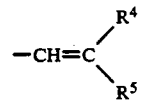

or a group of formula

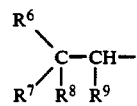

in which
$R^4$ represents a methyl group, a chlorine atom, a bromine atom, or a fluorine atom,
$R^5$ represents a methyl group, a trifluoromethyl group, a chlorine atom, a bromine atom, or a fluorine atom, and
$R^6$, $R^7$, $R^8$, and $R^9$, which can be the same or different, each represent a chlorine atom, a bromine atom, or a fluorine atom, and when
$R^2$ is a methyl group, $R^3$ represents a methyl group,
$R^{10}$ represents chlorine atom, a bromine atom, fluorine atom, a trifluoromethoxy group, a difluoromethoxy group, or a 3, 4-methylenedioxy group, Z represents an oxygen atom or a —CH2— group,
$R^{11}$ represents a lower alkoxy group having one to five carbon atoms, a chlorine atom, a bromine atom, or a fluorine atom,
$R^{12}$ represents a hydrogen atom or a lower alkyl group having one to two carbon atoms, and
$R^{13}$ represents a lower alkyl group having one to two carbon atoms or a trifluoromethyl group.

2. The method for controlling cockroaches according to claim 1, wherein said insecticidal compound is (RS-α-cyano-3-phenoxybenzyl (1R)-cis, trans-chrysanthemate.

3. The method for controlling cockroaches according to claim 1, wherein said insecticidal compound is (RS)-α-cyano-3-phenoxybenzyl (RS)-2-(4-chlorophenyl)-3-methylbutyrate.

4. The method for controlling cockroaches according to claim 1, wherein said insecticidal compound is 3-phenoxybenzyl (1R)-cis, trans-chrysanthemate.

5. The method for controlling cockroaches according to claim 1, wherein said insecticidal compound is 3-phenoxybenzyl (1RS)-cis, trans-3-(2,2-dichlorovinyl)-2,2-dimethylcyclopropanecarboxylate.

6. The method for controlling cockroaches according to claim 1, wherein the amount of phenylxylylethane is 0.2 to 5 parts by weight per part by weight of said insecticidal compound.

* * * * *